United States Patent
Zhu et al.

(10) Patent No.: US 11,839,705 B2
(45) Date of Patent: Dec. 12, 2023

(54) AIR PURIFICATION DEVICE ABLE TO KILL BACTERIA AND VIRUSES

(71) Applicant: SICHUAN UNIVERSITY, Sichuan (CN)

(72) Inventors: Huacheng Zhu, Sichuan (CN); Yang Yang, Sichuan (CN); Kama Huang, Sichuan (CN)

(73) Assignee: SICHUAN UNIVERSITY, Sichuan (CN)

( * ) Notice: Subject to any disclaimer, the term of this patent is extended or adjusted under 35 U.S.C. 154(b) by 304 days.

(21) Appl. No.: 17/165,914

(22) Filed: Feb. 2, 2021

(65) Prior Publication Data
US 2021/0178007 A1 Jun. 17, 2021

(51) Int. Cl.
*A61L 9/20* (2006.01)

(52) U.S. Cl.
CPC .............. *A61L 9/20* (2013.01); *A61L 2209/14* (2013.01)

(58) Field of Classification Search
None
See application file for complete search history.

(56) References Cited

FOREIGN PATENT DOCUMENTS

| CN | 203339113 U | * | 12/2013 |
| CN | 207540023 U | * | 6/2018 |
| RU | 2280617 C1 | * | 7/2006 |

* cited by examiner

Primary Examiner — Andrew Smyth

(57) ABSTRACT

An air purification device able to kill bacteria and viruses is provided, including an air channel, an air pump, a filtering device, and an electrodeless ultraviolet sterilization device. The electrodeless ultraviolet sterilization device is arranged inside the air channel and includes a microwave generator, an electrodeless ultraviolet tube, and a uniform radiator. The uniform radiator is a coaxial cable with gaps provided thereon. The electrodeless ultraviolet tube is a hollow columnar quartz tube. The coaxial cable is arranged in a hollow portion of the quartz tube. The coaxial cable is connected to the to microwave generator. The air purification device has a compact structure. Through arranging the electrodeless ultraviolet sterilization device inside the air channel, large-granular dust in the air is filtered, and meanwhile, bacteria and viruses in the air are effectively killed. Moreover, the present invention is safe and effective and has high sterilization efficiency and a low production cost.

14 Claims, 2 Drawing Sheets

AIR PURIFICATION DEVICE ABLE TO KILL BACTERIA AND VIRUSES

CROSS REFERENCE OF RELATED APPLICATION

The application claims priority under 35 U.S.C. 119(a-d) to CN 202010301868.0, filed Apr. 16, 2020.

BACKGROUND OF THE PRESENT INVENTION

Field of Invention

The present invention relates to a field of air purification, and more particularly to an air purification device able to kill bacteria and viruses.

Description of Related Arts

With the increasingly aggravated air pollution and the pursuit of life quality of people, the air purification device has become the standard equipment of homes, offices, and public places. The conventional air purification device in the prior art generally solves the problems of dust adsorption rate and working time. However, not only dust Its exists in the air, but also bacteria and viruses exist; in particular, in the hospital or during the disease outbreak, the virus-containing aerosols in the air frighten people. The ultraviolet sterilization technology in prior art needs to seal the room and needs a relatively long time for treatment, which cannot be applied in all places. Moreover, the ultraviolet sterilization technology has a huge laying cost and may damage the human body. The ozone sterilization technology in the prior art is not easy to operate, and any carelessness will cause a damage to the human body.

The microwave technology in the prior art can be applied in exciting the ultraviolet light. The frequently-used microwave generators are the magnetron and the solid-state source. Because the common waveguide has a relatively large size, the conventional microwave electrodeless ultraviolet lamp is not convenient to carry. Moreover, the conventional ultraviolet lamp has relatively small power; and, in the situation of relatively large airflow, the ultraviolet lamp generally cannot reach the sterilization standard. Thus, it is urgent to develop an air purification device able to solve the above problems.

SUMMARY OF THE PRESENT INVENTION

An object of the present invention is to provide an air purification device able to kill bacteria and viruses, which solves problems in prior art that conventional air purification devices are unable to kill the bacteria and the viruses.

Technical solutions of the present invention are described as follows.

An air purification device able to kill bacteria and viruses is provided, comprising an air channel, an air pump and a filtering device, and further comprising an electrodeless ultraviolet sterilization device, wherein: the electrodeless ultraviolet sterilization device is arranged inside the air channel; the electrodeless ultraviolet sterilization device comprises a microwave generator, an electrodeless ultraviolet tube and a uniform radiator; the uniform radiator is a coaxial cable with gaps provided thereon; the electrodeless ultraviolet tube is a columnar quartz tube which is hollow and comprises an interlayer, wherein mercury and argon are sealed in the interlayer; the coaxial cable is arranged in a hollow portion of the quartz tube; and the coaxial cable is connected to the microwave generator through a microwave transmission line.

Preferably, the electrodeless ultraviolet sterilization device is arranged behind the filtering device.

Preferably; the gaps are provided on an outer conductor of the coaxial cable; and external electric field distribution of the coaxial cable is uniform.

Preferably, the gaps are provided radially, transversely, or obliquely.

Preferably; a length of the coaxial cable is consistent with a length of the quartz tube.

Preferably; a short circuit surface is arranged at an end of the electrodeless ultraviolet tube, and the end is far away from the microwave generator.

Preferably, two ends of the coaxial cable and the electrodeless ultraviolet tube are sealed.

Preferably, the lengths of the coaxial cable and the electrodeless ultraviolet tube are 200 mm; and an amount of the gaps on the coaxial cable is 8.

Preferably, the coaxial cable is connected to the microwave generator through a microwave coaxial conversion device; the microwave coaxial conversion device comprises an output antenna connected to a magnetron, a coaxial connector connected to the coaxial cable, and a conversion cavity for energy feeding.

Preferably, the coaxial connector consists of an inner conductor and an outer conductor; the inner conductor of the coaxial connector is higher than the outer conductor of the coaxial connector; the inner conductor is a rivet structure; a radius of a part near the output antenna of the inner conductor is larger than that of a part far away from the output antenna of the inner conductor; the part near the output antenna is a rivet cap part; and the rivet cap part is chamfered.

According to the air purification device able to kill the bacteria and the viruses provided by the present invention, the microwave electrodeless ultraviolet lamp has the characteristics of small volume and high power, and makes the structure of the air purification device compact; through arranging the high-power electrodeless ultraviolet sterilization device inside the air channel of the air purification device, the large-granular dust in the air is filtered, and meanwhile, the bacteria and the viruses in the air are effectively killed; the present invention is safe and effective; through arranging the electrodeless ultraviolet lamp having the simple structure and uniform radiation, the present invention has the high sterilization efficiency and low production cost.

BRIEF DESCRIPTION OF THE DRAWINGS

To illustrate the technical solutions of the embodiments of the present invention or prior art more clearly, the accompanying drawings for describing the embodiments or prior art are simply described below. Apparently, the accompanying drawings in the following description are only some embodiments of the present invention, and persons of ordinary skill in the art can derive other drawings from the accompanying drawings without creative efforts.

In figures: 1: electrodeless ultraviolet tube; 2: interlayer; 3: hollow portion; 4: microwave transmission line; 5: coaxial cable; 6: gap; 7: magnetron; 8: conversion cavity; 9: inner conductor; 10: outer conductor; 11: rivet cap part; 12: air pump; 13: filtering net; 14: sterilization chamber; 15: outer conductor; 16: air channel; 17: microwave generator; 18: output antenna; and 19: short circuit surface.

DETAILED DESCRIPTION OF THE PREFERRED EMBODIMENT

Technical solutions in the preferred embodiment of the present invention will be clearly and completely described with accompanying drawings as follows. Apparently, the described preferred embodiment is merely a part of embodiments of the present invention, not all of the embodiments. Other embodiments obtained by one of ordinary skill in the art based on the preferred embodiment of the present invention without creative efforts are all encompassed in the protection scope of the present invention.

Figure 1:
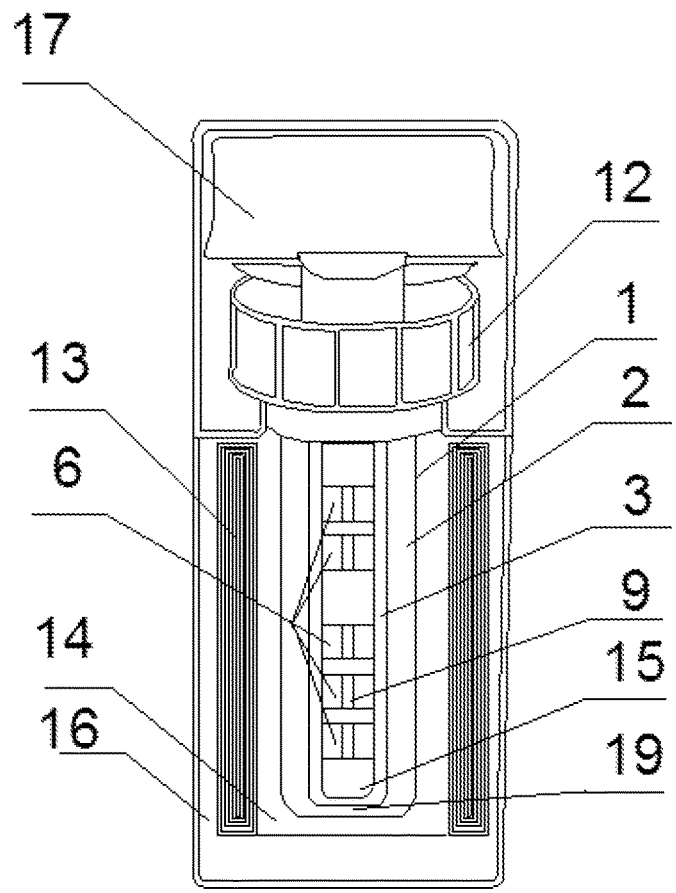
FIG. 1 is a structural sketch view of an air purification device able to kill bacteria and viruses according to the present invention.
Figure 2:
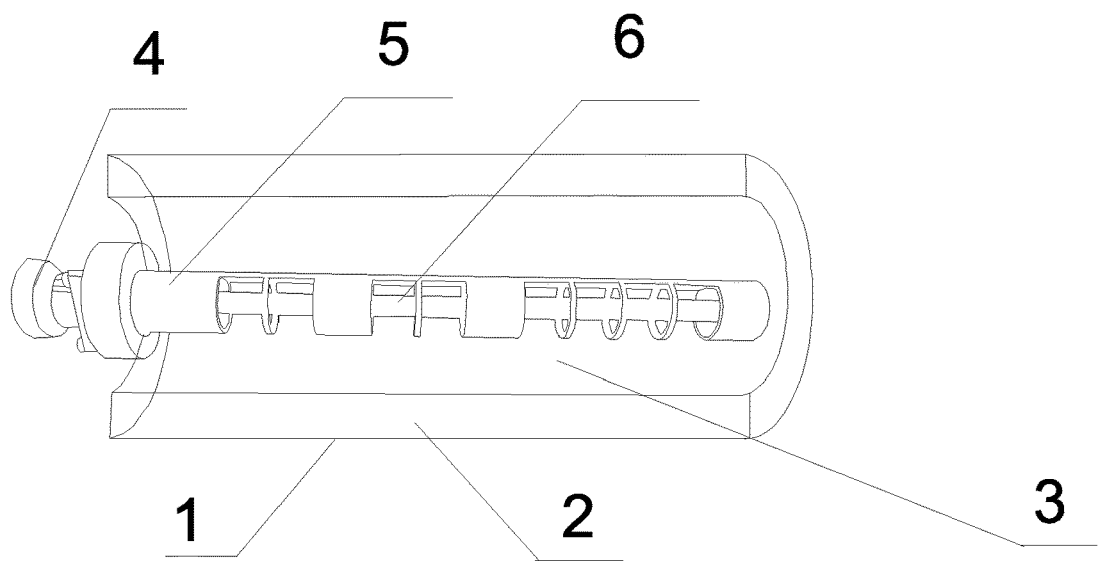
FIG. 2 is a first sectional view of an electrodeless ultraviolet tube according to the present invention.
Figure 3:
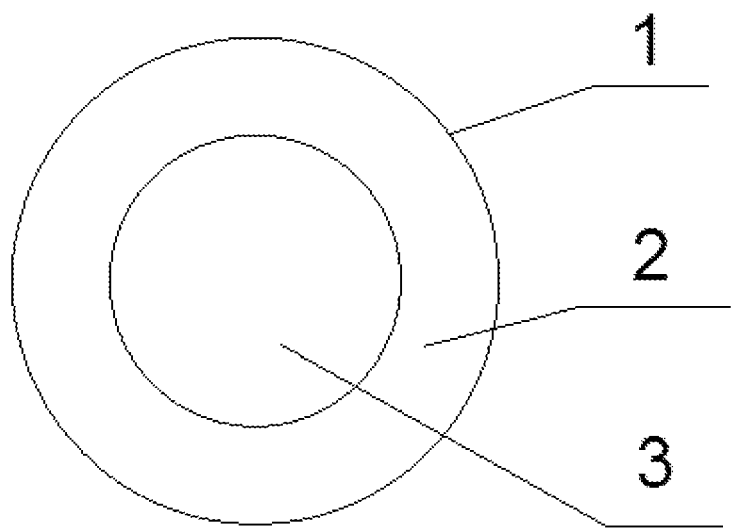
FIG. 3 is a second sectional view of the electrodeless ultraviolet tube according to the present invention.

According to the preferred embodiment of the present invention, an air purification device able to kill bacteria and viruses is provided, as shown in FIG. 1, comprising an air channel 16, an air pump 12 and a filtering device, and further comprising an electrodeless ultraviolet sterilization device, wherein: the filtering device is a filtering net 13, for filtering particulates and floccules in air; the electrodeless ultraviolet sterilization device is arranged inside the air channel; the electrodeless ultraviolet sterilization device comprises a microwave generator 17, an electrodeless ultraviolet tube 1 and a uniform radiator; the uniform radiator is a coaxial cable 5 with gaps 6 provided thereon, as shown in FIG. 2; the electrodeless ultraviolet tube 1 is a columnar quartz tube which is hollow and comprises an interlayer 2, wherein mercury and argon are sealed in the interlayer 2, as shown in FIG. 3; the coaxial cable 5 is arranged in a hollow portion 3 of the quartz tube; and the coaxial cable 5 is connected to the microwave generator 17 through a microwave transmission line 4.

Furthermore, the electrodeless ultraviolet sterilization device is arranged behind the filtering device.

Furthermore, the gaps 6 are provided on an outer conductor 15 of the coaxial cable 5; and external electric field distribution of the coaxial cable 5 is uniform.

Furthermore, the gaps 6 are provided radially, transversely, or obliquely.

Furthermore, a length of the coaxial cable 5 is consistent with a length of the quartz tube.

Furthermore, a short circuit surface 19 is arranged at an end of the electrodeless ultraviolet tube 1, wherein the end is far away from the microwave generator.

Furthermore, two ends of the coaxial cable 5 and the electrodeless ultraviolet tube 1 are sealed.

Furthermore, the lengths of the coaxial cable 5 and the electrodeless ultraviolet tube 1 are 200 mm; and an amount of the gaps 6 on the coaxial cable 5 is 8. Inside the coaxial cable, a current is transmitted along an axial direction of the coaxial cable 5 and along the radial gaps 6; the more cutting current, the greater energy coupled from the gaps; and an electromagnetic wave is radiated out from the coaxial gaps. With utilizing a FDTD (Finite-Difference Time-Domain) algorithm, according to a value of S11, the form, the size and the amount of the gaps on the coaxial cable 5 are optimized, so that uniform radiation of the microwave energy in the transmission direction of the whole coaxial cable 5 is finally realized. Because the microwave is transmitted from the feed port, the gap nearer the feed port is earlier coupled with the microwave energy; in order to guarantee that the coupled energy of the whole coaxial cable having the length of 200 mm in the axial direction is uniform, more gaps are provided at a position farther from the feed port.

Figure 4:
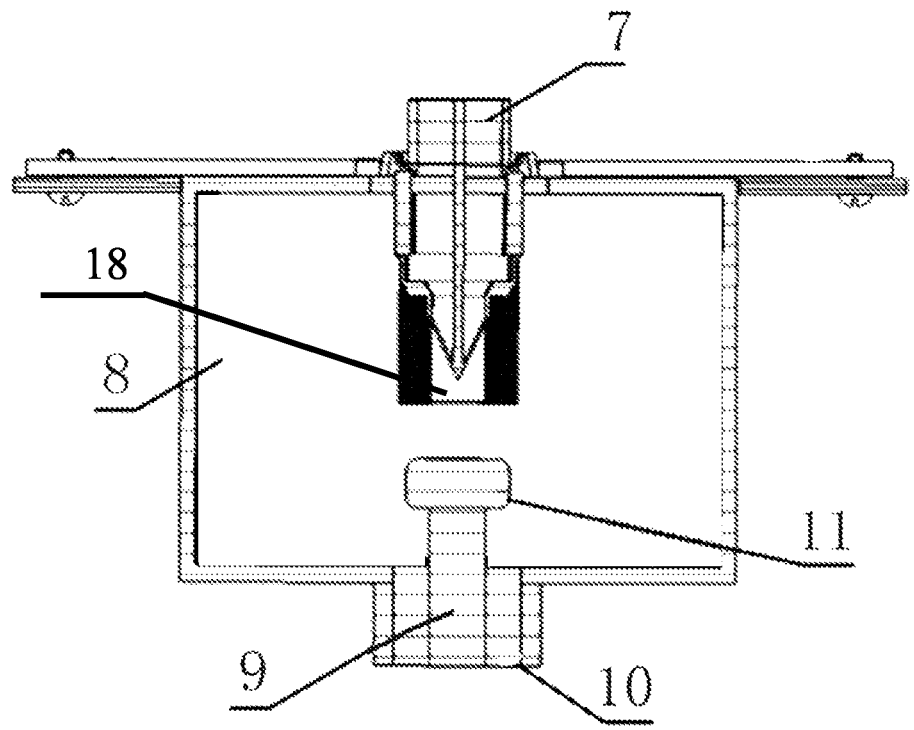
FIG. 4 is a structural sketch view of a microwave coaxial conversion device according to the present invention.

Furthermore, the coaxial cable 5 is connected to the microwave generator 17 through a microwave coaxial conversion device, wherein: the microwave coaxial conversion device comprises an output antenna 18 connected to a magnetron 7, a coaxial connector connected to the coaxial cable 5, and a conversion cavity 8 for energy feeding, as shown in FIG. 4. Furthermore, the coaxial connector consists of an inner conductor 9 and an outer conductor 10; the inner conductor 9 of the coaxial connector is higher than the outer conductor 10 of the coaxial connector; the inner conductor 9 is a rivet structure; a radius of a part near the output antenna 18 of the inner conductor 9 is larger than that of a part far away from the output antenna 18 of the inner conductor 9; the part near the output antenna 18 is a rivet cap part 11, and the rivet cap part 11 is chamfered.

For the microwave coaxial conversion device, through arranging the output antenna 18 connected to the magnetron 7 and the coaxial connector connected to the coaxial cable 5, the output of the microwave energy is conducted inside the conversion cavity 8. The microwave coaxial conversion device not only has a simple and compact structure and facilitates integration of a magnetron system, but also has a high microwave output efficiency and is hardly influenced by the load. Through arranging the rivet cap part 11, the point effect is effectively avoided.

The electrodeless ultraviolet sterilization device transmits the microwave generated by the magnetron 7 to the uniform radiator through the microwave transmission line 4; the uniform radiator uniformly radiates the microwave to the hollow portion 3 of the quartz tube through the gaps; the microwave radiated through the gaps uniformly excites the mercury and the argon in the interlayer 2 to generate the ultraviolet.

During use, the power supply is switched on, and the air pump 12 pumps air in the space into the air channel 16, so that air passes through the filtering net 13 and the electrodeless ultraviolet sterilization device. For the electrodeless ultraviolet sterilization device, the electromagnetic wave radiation is conducted with the opened non-uniform gaps through the L29 head connected to the coaxial cable 5 by the microwave generator 17 namely the solid-state source. The farther the distance from the microwave feed port, the more gaps 6 provided on the coaxial cable 5. Particularly, with utilizing the FDTD algorithm, according to the value of S11 and whether the electric field distribution outside the quartz tube is uniform, the gaps are provided. When the gaps 6 uniformly radiate the electromagnetic wave in the electrodeless ultraviolet lamp, the uniform illumination of the electrodeless ultraviolet lamp is achieved.

When the input power is 500 W, the port microwave reflection coefficient S11 passing through the simulation feeding port is smaller than −10 dB. It can be seen that: the electric field intensity at the ultraviolet tube can reach above 3000 V/m; the electric field intensity in all directions is uniform; and the electric field at all positions of the whole ultraviolet tube is uniform. The coaxial cable 5 connected to the microwave generator is arranged in the hollow portion 3 of the hollow electrodeless ultraviolet tube 1; the non-uniform gaps 6 radiate the electromagnetic wave, and form the uniformly distributed electric field inside the quartz tube; so as to uniformly radiate the electromagnetic wave to the electrodeless ultraviolet tube 1 in all directions.

For the air after passing through the filtering net 13 and the sterilization chamber 14, not only the large-granular dust in the air is removed, but also the bacteria and the viruses in the air are killed by the ultraviolet light.

According to the air purification device able to kill the bacteria and the viruses provided by the present invention, the microwave electrodeless ultraviolet tube 1 has the characteristics of small volume and high power, and makes the structure of the air purification device compact; through arranging the high-power electrodeless ultraviolet sterilization device inside the air channel of the air purification device, the large-granular dust in the air is filtered, and meanwhile the bacteria and the viruses in the air are effectively killed; the present invention is safe and effective; through arranging the electrodeless ultraviolet lamp having the simple structure and uniform radiation, the present invention has the high sterilization efficiency and low production cost.

Obviously, various corresponding changes and modifications can be made by one of ordinary skill in the art based on the present invention without departing from the spirit and essence of the present invention. These corresponding changes and modifications should be all encompassed in the protection scope of the claims of the present invention.

What is claimed is:

1. An air purification device able to kill bacteria and viruses, comprising an air channel, an air pump and a filtering device, and further comprising an electrodeless ultraviolet sterilization device, wherein: the electrodeless ultraviolet sterilization device is arranged inside the air channel; the electrodeless ultraviolet sterilization device comprises a microwave generator, an electrodeless ultraviolet tube and a uniform radiator; the uniform radiator is a coaxial cable with gaps provided thereon; the electrodeless ultraviolet tube is a columnar quartz tube which is hollow and comprises an interlayer, wherein mercury and argon are sealed in the interlayer; the coaxial cable is arranged in a hollow portion of the quartz tube; the coaxial cable is connected to the microwave generator through a microwave transmission line;

the coaxial cable is connected to the microwave generator through a microwave coaxial conversion device;

the microwave coaxial conversion device comprises an output antenna connected to a magnetron, a coaxial connector connected to the coaxial cable, and a conversion cavity for energy feeding;

the coaxial connector consists of an inner conductor and an outer conductor;

the inner conductor of the coaxial connector is higher than the outer conductor of the coaxial connector; and the inner conductor is a rivet structure, wherein a radius of a first part of the inner conductor is larger than that of a second part of the inner conductor, the first part of the inner conductor is closer to the output antenna than the second part of the inner conductor, the first part of the inner conductor is a rivet cap part, and the rivet cap part is chamfered.

2. The air purification device, as recited in claim 1, wherein the electrodeless ultraviolet sterilization device is arranged behind the filtering device.

3. The air purification device, as recited in claim 1, wherein the gaps are provided on an outer conductor of the coaxial cable; and external electric field distribution of the coaxial cable is uniform.

4. The air purification device, as recited in claim 2, wherein the gaps are provided on an outer conductor of the coaxial cable; and external electric field distribution of the coaxial cable is uniform.

5. The air purification device, as recited in claim 3, wherein the gaps are provided radially, transversely, or obliquely.

6. The air purification device, as recited in claim 4, wherein the gaps are provided radially, transversely, or obliquely.

7. The air purification device, as recited in claim 5, wherein a length of the coaxial cable is equal to a length of the quartz tube.

8. The air purification device, as recited in claim 6, wherein a length of the coaxial cable is equal to a length of the quartz tube.

9. The air purification device, as recited in claim 7, wherein: a short circuit surface is arranged at an end of the electrodeless ultraviolet tube.

10. The air purification device, as recited in claim 8, wherein: a short circuit surface is arranged at an end of the electrodeless ultraviolet tube.

11. The air purification device, as recited in claim 9, wherein: two ends of the coaxial cable and the electrodeless ultraviolet tube are sealed.

12. The air purification device, as recited in claim 10, wherein: two ends of the coaxial cable and the electrodeless ultraviolet tube are sealed.

13. The air purification device, as recited in claim 11, wherein: the lengths of the coaxial cable and the electrodeless ultraviolet tube are 200 mm; and an amount of the gaps on the coaxial cable is 8.

14. The air purification device, as recited in claim 12, wherein: the lengths of the coaxial cable and the electrodeless ultraviolet tube are 200 mm; and an amount of the gaps on the coaxial cable is 8.

\* \* \* \* \*